(12) United States Patent
Radulescu et al.

(10) Patent No.: US 11,801,401 B2
(45) Date of Patent: *Oct. 31, 2023

(54) HIGH INTENSITY FOCUSED ULTRASOUND TRANSDUCER OPTIMIZATION

(71) Applicant: Profound Medical Inc., Mississauga (CA)

(72) Inventors: Emil G. Radulescu, Ossining, NY (US); Gosta Jakob Ehnholm, Helsinki (FI); Ramon Q. Erkamp, Purdys, NY (US); I. A. Julius Koskela, Helsinki (FI); Shunmugavelu D. Sokka, Belmont, MA (US); Erkki T. Vahala, Hyvinkaa (FI); Max Oskar Kohler, Espoo (FI)

(73) Assignee: Profound Medical Inc., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/820,098

(22) Filed: Aug. 16, 2022

(65) Prior Publication Data

US 2022/0395709 A1 Dec. 15, 2022

Related U.S. Application Data

(60) Division of application No. 16/102,970, filed on Aug. 14, 2018, which is a continuation of application No.
(Continued)

(51) Int. Cl.
*A61N 7/02* (2006.01)
*A61N 7/00* (2006.01)
(Continued)

(52) U.S. Cl.
CPC .......... *A61N 7/02* (2013.01); *A61B 2034/104* (2016.02); *A61B 2034/105* (2016.02);
(Continued)

(58) Field of Classification Search
None
See application file for complete search history.

(56) References Cited

U.S. PATENT DOCUMENTS

| 5,590,657 A | 1/1997 | Cain et al. |
| 5,806,521 A | 9/1998 | Morimoto et al. |

(Continued)

FOREIGN PATENT DOCUMENTS

| EP | 0998217 B1 | 1/2009 |
| WO | 2006018686 A1 | 2/2006 |

(Continued)

OTHER PUBLICATIONS

"High Intensity Focused Ultrasound (HIFU)", American Chronicle, http://www.americanchronicle.com/articles/view/117740, Nov. 5, 2009, pp. 1-3.

(Continued)

*Primary Examiner* — Katherine L Fernandez
(74) *Attorney, Agent, or Firm* — Intrinsic Law Corp.

(57) ABSTRACT

When planning magnetic resonance (MR) guided high intensity focused ultrasonic (HIFU) therapy, HIFU transducer element parameters are optimized as a function of 3D MR data describing a size, shape, and position of a region of interest (ROI) (146) and any obstructions (144) between the HIFU transducer elements and the ROI (146). Transducer element phases and amplitudes are adjusted to maximize HIFU radiation delivery to the ROI (146) while minimizing delivery to the obstruction (144). Additionally or alternatively, transducer elements are selectively deactivated if the obstruction (144) is positioned between the ROI (146) and a given transducer element.

2 Claims, 11 Drawing Sheets

Related U.S. Application Data

13/515,519, filed as application No. PCT/IB2010/055640 on Dec. 7, 2010, now Pat. No. 10,058,717.

(60) Provisional application No. 61/290,268, filed on Dec. 28, 2009.

(51) Int. Cl.
*A61B 34/10* (2016.01)
*A61B 90/00* (2016.01)

(52) U.S. Cl.
CPC . *A61B 2090/374* (2016.02); *A61N 2007/0065* (2013.01); *A61N 2007/0078* (2013.01); *A61N 2007/0095* (2013.01)

(56) References Cited

U.S. PATENT DOCUMENTS

| | | | |
|---|---|---|---|
| 6,039,689 | A | 3/2000 | Lizzi |
| 6,128,522 | A * | 10/2000 | Acker ............ A61B 34/76 335/298 |
| 7,520,856 | B2 | 4/2009 | Vaezy et al. |
| 9,177,543 | B2 | 11/2015 | Vitek et al. |
| 2004/0039312 | A1 | 2/2004 | Hillstead et al. |
| 2004/0059265 | A1 | 3/2004 | Candy et al. |
| 2006/0058671 | A1 * | 3/2006 | Vitek ............ A61N 7/02 600/447 |
| 2006/0058678 | A1 | 3/2006 | Vitek et al. |
| 2008/0015435 | A1 | 1/2008 | Cribbs et al. |
| 2008/0183077 | A1 | 7/2008 | Moreau-Gobard et al. |
| 2008/0200806 | A1 * | 8/2008 | Liu ............ A61N 7/02 600/439 |
| 2008/0319375 | A1 | 12/2008 | Hardy |
| 2009/0012514 | A1 | 1/2009 | Moonen et al. |
| 2009/0054772 | A1 | 2/2009 | Lin et al. |
| 2009/0088623 | A1 | 4/2009 | Vortman et al. |
| 2009/0230823 | A1 | 9/2009 | Kushculey et al. |
| 2010/0030076 | A1 | 2/2010 | Vortman et al. |
| 2012/0253176 | A1 | 10/2012 | Dumoulin |

FOREIGN PATENT DOCUMENTS

| | | |
|---|---|---|
| WO | 2008120117 A2 | 10/2008 |
| WO | 2008143998 A1 | 11/2008 |
| WO | 2009081339 A1 | 7/2009 |

OTHER PUBLICATIONS

J.F. Aubry et al., "Transcostal High-Intensity-Focused Ultrasound: Ex Vivo Adaptive Focusing Feasibility Study", Physics in Medicine and Biology, May 12, 2008, pp. 2937-2951, vol. 53, IOP Publishing, U.K.

Y.Y. Botros et al., "Two-Step Hybrid Virtual Array-Ray (VAR) Technique for Focusing Through the Rib Cage", IEEE Transactions on Ultrasonics, Ferroelectrics, and Frequency Control, Jul. 1998, pp. 989-1000, vol. 45, IEEE.

D. R. Daum et al., "In Vivo Demonstration of Noninvasive Thermal Surgery of the Liver and Kidney Using an Ultrasonic Phased Array", Ultrasound in Medicine and Biology, Mar. 29, 1999, pp. 1087-1098, vol. 25, No. 7, World Federation for Ultrasound in Medicine and Biology, USA.

D.A. Guenther et al., "A Method for Accurate In Silico Modeling of Ultrasound Tranducer Arrays", Ultrasonics, 2009, pp. 404-412, vol. 49, Elsevier B.V.

C. Lafon et al., "Interstitial Devices for Treating Deep Seated Tumors", AIP Conference Proceedings, May 8, 2006, pp. 365-369, vol. 829, American Institute of Physics.

V. Le Floch et al., "Ultrasound Simulation in the Distal Radius Using Clinical High-Resolution Peripheral-CT Images", Ultrasound Med Biol., Aug. 2008, pp. 1317-1326, vol. 34, No. 8.

M. Rata et al., "Optimization of the Thermal Dosimetry for Endocavitary HICU Ablation of Sectorial Digestive Tumours", AIP Conference Proceedings., May 21, 2007, pp. 278-282, vol. 911, American Institute of Physics.

N. Urban et al., "Use of a Stochastic Simulation Model to Identify an Efficient Protocol for Ovarian Cancer Screening", Contemporary Clinical Trials, Jun. 1997, pp. 251-270, vol. 18, No. 3, Elsevier Science, Inc.

R. McGough et al., "Treatment Planning for Hyperthermia with Ultrasound Phased Arrays," IEEE Transactions on Ultrasonics, Ferroelectrics, and Frequency Control, vol. 43, No. 6, pp. 1074-1084 (1996).

* cited by examiner

HIGH INTENSITY FOCUSED ULTRASOUND TRANSDUCER OPTIMIZATION

CROSS-REFERENCE TO RELATED APPLICATIONS

This application is a divisional of U.S. patent application Ser. No. 16/102,970 filed Aug. 14, 2018, entitled "High Intensity Focused Ultrasound Transducer Optimization", which is a continuation of U.S. patent application Ser. No. 13/515,519 filed Jun. 13, 2012 (now U.S. Pat. No. 10,058,717), entitled "High Intensity Focused Ultrasound Transducer Optimization," which is the U.S. National Stage of International Application No. PCT/IB2010/055640 filed Dec. 7, 2010, entitled "High Intensity Focused Ultrasound Transducer Optimization," which claims the benefit of U.S. Provisional Application Ser. No. 61/290,268 filed Dec. 28, 2009, each of which are hereby incorporated herein by reference in their entirety.

DESCRIPTION

The present application finds particular utility in magnetic resonance (MR)-guided high intensity focused (HIFU) ablation procedures and systems. However, it will be appreciated that the described technique(s) may also find application in other types of therapy planning systems, other image guided therapy systems, and/or other medical applications.

Liver cancer is one of the most usual tumor types, and is especially difficult to operate because it tends to bleed strongly. Ablative procedures have therefore become common for its treatment, including thermal ablation with radio frequency (RF) or laser probes, cryoblation, etc.

The use of High Intensity Focused Ultrasound (HIFU) has gradually become more popular. One reason is that MR imaging can be used for monitoring tissue temperature during the procedure, making it less risky. For liver ablation there are two major problems: The liver has a lot of blood flow, and it moves around with the patient respiration. Another problem is that the liver is situated behind the ribs, which obstruct HIFU transmission.

Generally speaking, one problem associated with MR-guided HIFU procedures is that it is difficult to distribute the applied heat in the right places: On one hand the ROI, e.g. a tumor, needs to be ablated. On the other hand, the regions in front of it (near field), or behind it (far field), as seen from transducer, need to be preserved. In the case of the liver this problem is aggravated by the fact that the liver is efficiently cooled by the blood flow, increasing the demand on ultrasonic power, and at the same time the ribs limit accessibility to the ROI. The rib problem is twofold: First, the part of the beam hitting the ribs cannot reach the ROI, and second, the ribs are sensitive to ultrasonic radiation because they absorb it effectively and therefore easily overheat.

Classical planning procedures are mainly designed for sonication of organs that can be reached directly without beaming between ribs, e.g. the uterus. The focal spot of the transducer is steered to the ROI. In the most sophisticated systems both mechanical, using motors, and electronic steering, using phased transducer element arrays, are used.

Presently, the state of the art in treatment planning is that a planning software tool is used to describe the desired transducer position and treatment cells using MRI images from the patient. The software visualizes the acoustic path on top of the MRI images in order to reveal whether any critical organs are located in the beam path or within the safety margins. The acoustic beam is modeled simply as a geometric cone from the transducer to the focal point and into the far field. During treatment, low-energy sonications are used to detect and manually correct spatial deviation from the targeted focus, and thermal monitoring is used as a feedback to control the thermal heating.

General numerical methods for solving wave propagation are known in the literature. In the field of medical ultrasound, the most prominent approaches are time-domain based methods, the finite-element method, and the various derivates of the Rayleigh integral.

In conventional treatment and treatment planning techniques, the acoustic path is assumed to be through water (e.g., a water phantom). However, there are various materials and tissues with different acoustic properties along the acoustic path through a human subject or patient. In particular, the role of the subcutaneous fat as a source of acoustic distortion is well known. Refraction at interfaces causes shift of the acoustic focus from the targeted position, and phase deviation due to different acoustic path lengths degrades the sharpness of the spot. These problems are conventionally dealt with using trial-and-error manual corrections and thermal feedback. These tasks can be alleviated by properly modeling the acoustic path.

A conventional treatment plan is generated using geometrical cones, so that the whole relevant volume is covered by the ultrasonic waves. However, often significantly-distorting objects (i.e. obstructions) are located along the acoustic path, such as bones. Bones give a rise to reflections and wave diffraction, distorting the shape of the focus, and creating potential detriment to both the patient and the ultrasonic transducer.

For simulation techniques with accurate numerical methods, such as a finite element method or a Rayleigh integral, the geometry of the problem is typically described as a discrete mesh, consisting of finite geometric primitives such as triangles. The dimensions of the primitives are a fraction of the wavelength. A common characteristic of the acoustic modeling problem is that the considered structures are relatively large in terms of acoustic wavelengths, resulting in correspondingly large meshes. Details vary according to the specific numerical method employed, but common to all these methods are interactions of the small primitives with each other. For large meshes, this results in such long simulation times that the technique may not be cost-effective in an interactive fashion. For instance, one popular way to use such techniques is to use a working day to plan and prepare the simulation task, and to perform the actual computation overnight or during a weekend.

There is an unmet need in the art for systems and methods that facilitate automated optimization of HIFU transducer element properties to exploit intercostal space in the patient as an ablation path, and the like, thereby overcoming the deficiencies noted above.

In accordance with one aspect, a therapy planning tool that facilitates magnetic resonance (MR) guided high intensity focused ultrasonic (HIFU) ablation planning includes a processor that executes computer-executable instructions for optimizing HIFU transducer element transmission, the instructions comprising evaluating transducer data including transducer element position, geometry, and acoustic parameter information. The instructions further include evaluating 3D MR data including ROI data describing a size, shape, and position of a region of interest (ROI) to be ablated, and obstruction data describing a size, shape, and position of an obstruction between one or more HIFU transducer elements and the ROI. Additionally, the instructions include executing an optimizer that maximizes HIFU waveform delivery the ROI while minimizing HIFU waveform delivery to the obstruction and surrounding tissue. The planning tool further includes a memory that stores the computer-executable instructions, the transducer data, MR data, and a plurality of optimized HIFU parameters.

According to another aspect, a method of magnetic resonance (MR) guided high intensity focused ultrasonic (HIFU) ablation planning includes evaluating transducer data including transducer element position, geometry, and acoustic parameter information, and evaluating 3D MR data including ROI data describing a size, shape, and position of a region of interest (ROI) to be ablated, and obstruction data describing a size, shape, and position of an obstruction between one or more HIFU transducer elements and the ROI. The method further includes executing an optimizer that maximizes HIFU waveform delivery the ROI while minimizing HIFU waveform delivery to the obstruction and surrounding tissue.

According to another aspect, a method of performing an in-situ sonication simulation for an MR-guided high intensity focused ultrasound (HIFU) ablation procedure includes generating a patient-specific acoustic path model, presenting the acoustic path model to a user via a user interface, and receiving user input regarding adjustments to at least one of a position of one or more HIFU transducer elements and a transmission phase and amplitude of the one or more HIFU transducer elements. The method further includes simulating a HIFU sonication of a region of interest (ROI) using the acoustic path model and the user input.

One advantage is reduction of HIFU exposure in healthy tissue.

Another advantage resides in maximizing HIFU exposure in the ROI.

Another advantage resides in using acoustic simulations to model focal shape and monitor stray fields.

Another advantage resides in the ability to avoid excessive heating of sensitive tissues.

Still further advantages of the subject innovation will be appreciated by those of ordinary skill in the art upon reading and understanding the following detailed description.

The drawings are only for purposes of illustrating various aspects and are not to be construed as limiting.

Systems and methods are disclosed herein for optimizing selection of HIFU transducer transmitting parameters and position during MR-guided tissue ablation procedures that utilize intercostal spaces, such as liver ablation. The optimization procedure accounts for the HIFU transducer position, geometry and acoustic parameters. It also accounts for the ablation region of interest (ROI) size and position as well as ribs' locations in 3D. The ribs' locations are determined through segmentation of high resolution MR data. The optimization procedure yields the amplitude and phase for each element of the transducer, as well as a series of five degrees of freedom transducer locations (three dimensions plus pitch and yaw) together with a corresponding list of deactivated elements per position. The amplitudes and phases assure maximum heat deposition in the ROI and minimum on the ribs. It should be noted that there is no direct element shutoff but rather optimal amplitudes and phases applied to all transducer elements. In addition, the optimization procedure yields superposition amplitude and phase results that ablate multiple zones of the ROI concurrently, minimizing the overall therapy time.

In another embodiment, each transducer position is associated with a given HIFU exposure time and energy such that after sonication from all positions the entire ROI is ablated. The transducer positions can be sorted in the descending order of their ROI coverage so that the treatment starts from the position with best coverage. In another embodiment, heating in superficial skin layers can be minimized by sorting the transducer positions such that there is minimal overlap between consecutive active aperture footprints.

Figure 1:
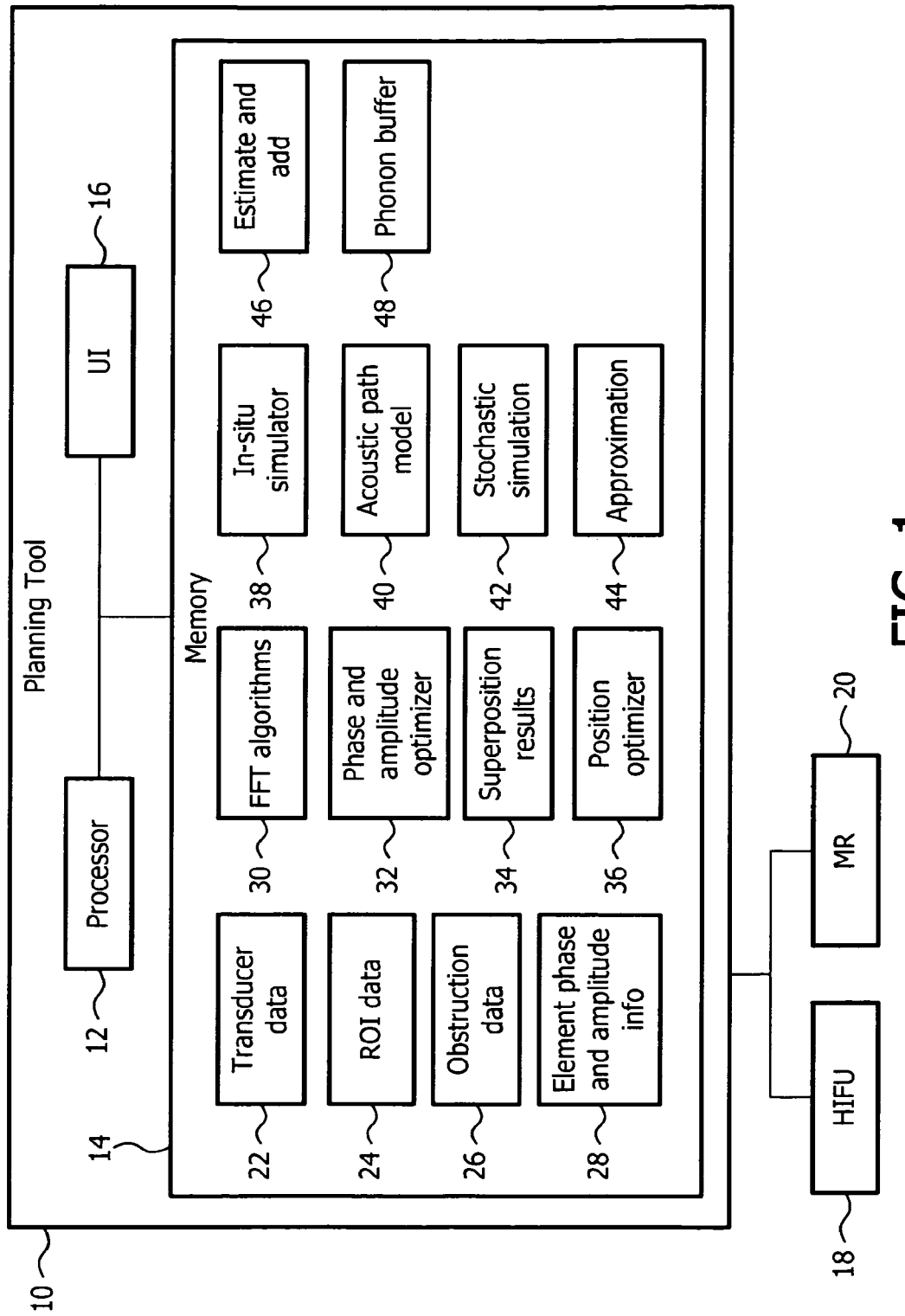
FIG. 1 illustrates a planning tool that facilitates optimizing transducer element phase, amplitude, position, etc., and performing fast acoustic simulations in situ during ultrasonic treatment planning.

With reference to FIG. 1, a planning tool 10 is illustrated that facilitates optimizing transducer element phase, amplitude, position, etc., and performing fast acoustic simulations in situ during ultrasonic treatment planning. The tool 10 includes a processor 12 that executes, and a memory or computer-readable medium 14 that stores, computer-executable instructions for performing the various functions, methods and/or algorithms described herein. In one embodiment, the processor 12 includes a parallel processing architecture. The tool further includes a user interface (UI) 16 (e.g., a monitor, computer terminal, workstation, etc.) via which information is presented to and received from a user or operator. The tool is coupled to each of a high-intensity focused ultrasound (HIFU) device 18 and a magnetic resonance (MR) scanner 20.

The memory includes HIFU transducer data 22 or information, including transducer element position, geometry, and acoustic parameter information. ROI data 24 and obstruction data 26 are provided by the MR scanner, and stored in the memory as well. The ROI data describes a 3D size and shape of a region of interest (e.g., an ablation target), while the obstruction data describes a position or location and shape of an obstruction (e.g., a rib or other bone) between the transducer elements and the ROI. The HIFU device also provides transducer element phase and amplitude information 28, which is stored in the memory. The processor analyzes spatial impulse response information (e.g., from probes coupled to the ROI and obstruction), and executes a Fourier transform algorithm 30 for a given continuous wave frequency, which is input into a phase and amplitude optimizer 32 (e.g., computer-executable instructions that are executed by the processor 12). The processor also generates an initial solution for an amplitude and phase at which each transducer element is to transmit, and an objective function that is input to the phase an amplitude optimizer, which then generates an optimal solution for the phase and amplitude of each transducer to ablate the ROI while minimizing heat transfer to surrounding tissue and/or the obstruction(s). Additionally, the memory stores superposition results 34, which are generated by the processor 12 to superposition the amplitude and phase of multiple elements in order to facilitate concurrent ablation of multiple zones of the ROI. These aspects are described in greater detail with regard to FIGS. 2-5, below.

The memory also includes a position optimizer 36 (e.g., a set of computer-executable instructions or the like) that receives transducer data 22 related to a position of each transducer element along a surface of a patient, and relative to the ROI and any obstruction. The position optimizer, when executed by the processor 12, deactivates transducer elements that have a line of sight that passes through an obstruction on the way to the ROI. In this manner, only elements with an unimpeded line of sight to the ROI remain active and transmit during ablation. These aspects are described further with regard to FIGS. 6-8, below.

According to another embodiment, the memory includes an in situ ablation simulator 38 (e.g., computer-executable instructions that are executed by the processor 12) that performs fast acoustic simulations during in situ treatment planning, one which employs an acoustic path model 40 of the patient anatomy during an ablation simulation. Three suitable algorithms are described herein for carrying out the in situ simulation, including a stochastic simulation algorithm 42, an approximation algorithm 44, and an estimation algorithm 46. The stochastic simulation algorithm employs a phonon buffer 48 that stores phonon information during the simulation procedure. These features are described in greater detail with regard to FIGS. 9-11.

In one embodiment, the acoustic path model includes a water tank, Mylar foil, gel pad, and patient anatomy. The acoustic parameters, typically wave velocity, wave attenuation, and tissue density, are specified for each point of the simulation volume. This is done by segmenting the volume into homogeneous subvolumes, and specifying a set of acoustic parameters for each subvolume. In one embodiment, a user provides the segmentation information manually based on the planning images (e.g., generated using the MR scanner 20). For example, for fibroid treatment the location and approximate thickness of the subcutaneous fat layer may be useful. In another embodiment, automatic segmentation algorithms (not shown) are used to do the segmentation from the planning images taken in situ.

In other embodiments, such as in applications where either the quality of the MRI images or the computational requirements make in situ automatic segmentation unfeasible, segmentation can be done offline based on previously generated images. Additionally, imaging modalities other than MRI can be used as a basis for segmentation.

To complete the segmentation, each subvolume is provided specific acoustic parameters. In one embodiment, the user enters the parameter values using the UI 16. The values can be determined based on the tissue from a table of typical values.

FIGS. 2-5 and the related description relate to optimization of transducer transmission parameters to exploit intercostal spacing during MR-guided tissue ablation.

Figure 2:
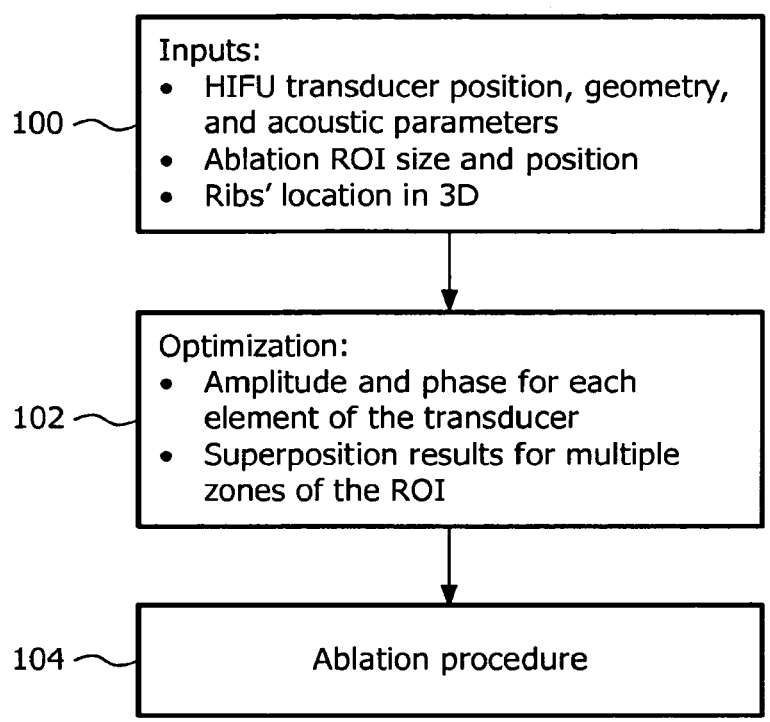
FIG. 2 illustrates a process flow for optimizing transmission parameters (e.g., amplitudes and phases) corresponding to a given HIFU transducer position, as well as geometry and acoustic parameters while accounting for the ablation ROI size and position and the ribs' locations.

FIG. 2 illustrates a process flow for optimizing transmission parameters (e.g., amplitudes and phases) corresponding to a given HIFU transducer position, as well as geometry and acoustic parameters while accounting for the ablation ROI size and position and the ribs' locations. In addition, the optimization process of FIG. 2 optimizes the overall therapy time by providing amplitudes and phases that facilitate concurrent ablation of multiple zones of the ROI. At 100, several types of input information are received (e.g., by a processor performing the optimization). The input information includes HIFU transducer position, geometry, and acoustic parameters, as well as ablation ROI size and position. The input information also includes 3D rib position information.

At 102, optimization is performed, and includes optimizing an amplitude and phase for each of a plurality of transducer elements. The optimization further includes generating and/or optimizing superposition amplitude and phase results for multiple zones of the ROI, permitting concurrent ablation of multiple zones of the ROI and reducing ablation procedure duration. This step is further described with regard to FIG. 3. At 104, an ablation procedure is performed using the optimized amplitude and phase information and the superposition results.

The method of FIG. 2 thus provides an optimization technique for selection of HIFU transducer transmitting parameters during MR-guided tissue ablation procedures that utilize intercostal spaces, such as liver ablation. The optimization procedure yields the amplitude and phase for each element of the HIFU transducer. The optimized amplitudes and phases assure maximum heat deposition in the ROI and minimum heat deposition on the ribs. It will be noted that, in one embodiment, there need be no direct element shutoff, but rather optimal amplitudes and phases may be applied to all transducer elements.

Figure 3:
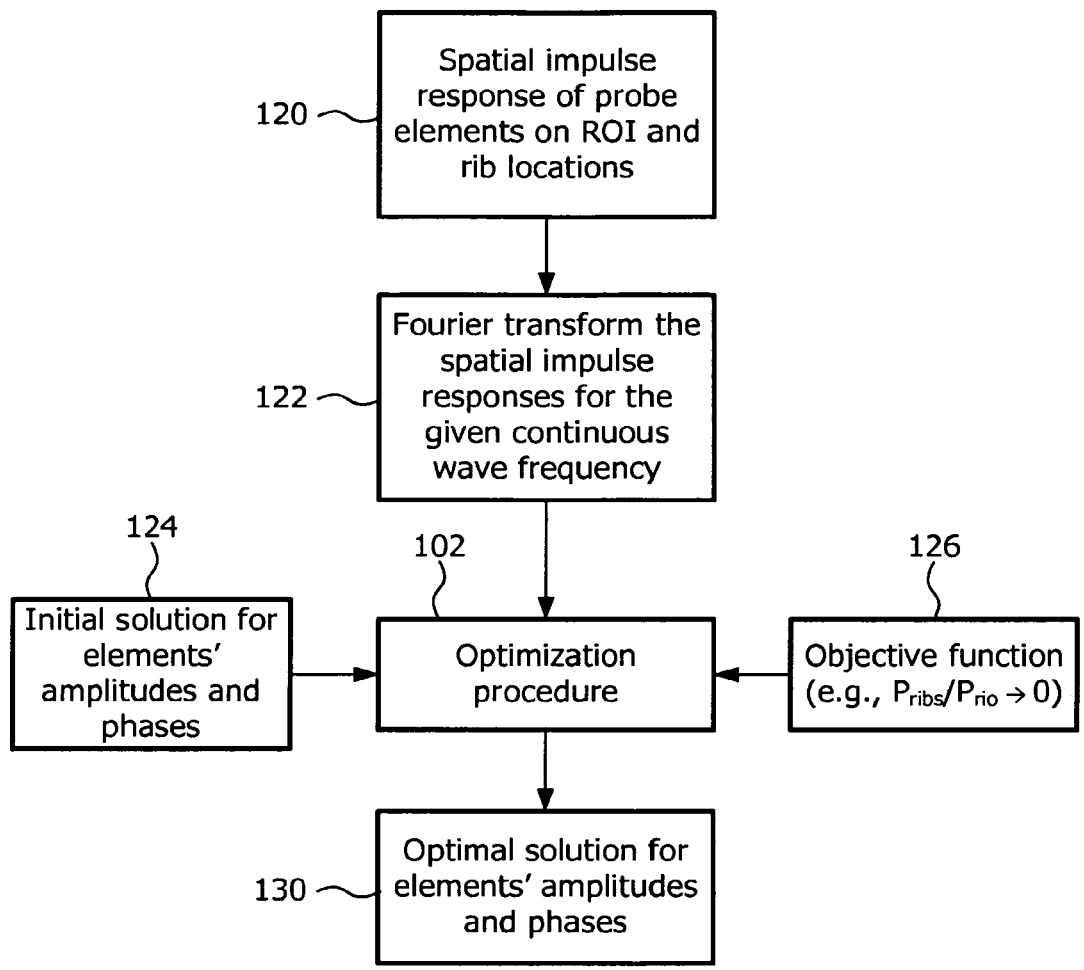
FIG. 3 illustrates a process flow for the optimization procedure based on a spatial impulse response technique.

FIG. 3 illustrates a process flow for the optimization procedure based on a spatial impulse response technique. At 120, spatial impulse responses are calculated for the transducer probe elements on a grid of points in the ROI and at the ribs locations. For clarity, FIG. 4 (below) shows the HIFU transducer, the ribs' positions and ablation ROI. At 122, a continuous wave (CW) solution is obtained by performing a Fourier transform on the impulse responses for the given CW frequency (acoustic linear propagation is assumed for low MI's). At 124, an initial solution for elements' amplitudes and phases is provided to the optimization procedure 102. E.g., for a transducer with 128 elements, 256 values are provided. At 126, an objective function is determined by the ratio of acoustic pressure in the ROI and the acoustic pressure at the ribs' level. Using the input information from 122, 124, and 126, the optimization function 102 is carried out to minimize the objective function. At 128, an optimal solution for elements' amplitudes and phases is provided. It will be appreciated that similar approaches developed in the frequency domain can be used, such as using back-propagation from ROI to transducer aperture elements and accounting for rib position.

Figure 4:
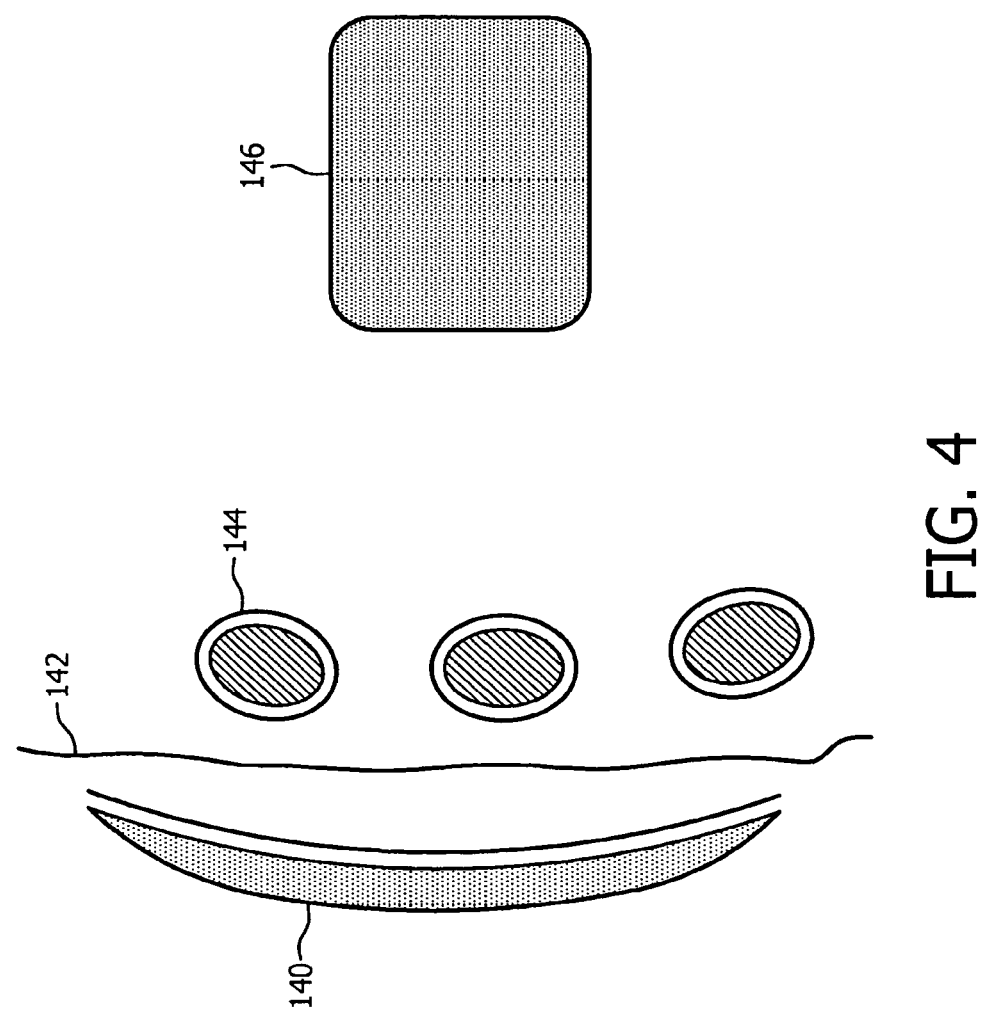
FIG. 4 illustrates an example of a HIFU transducer array positioned adjacent a patient's skin, with a plurality of ribs impeding the transmission of ultrasonic waves to an ROI to be ablated.

FIG. 4 illustrates an example of a HIFU transducer array 140 positioned adjacent a patient's skin 142, with a plurality of ribs 144 impeding the transmission of ultrasonic waves to an ROI 146 to be ablated.

Figure 5:
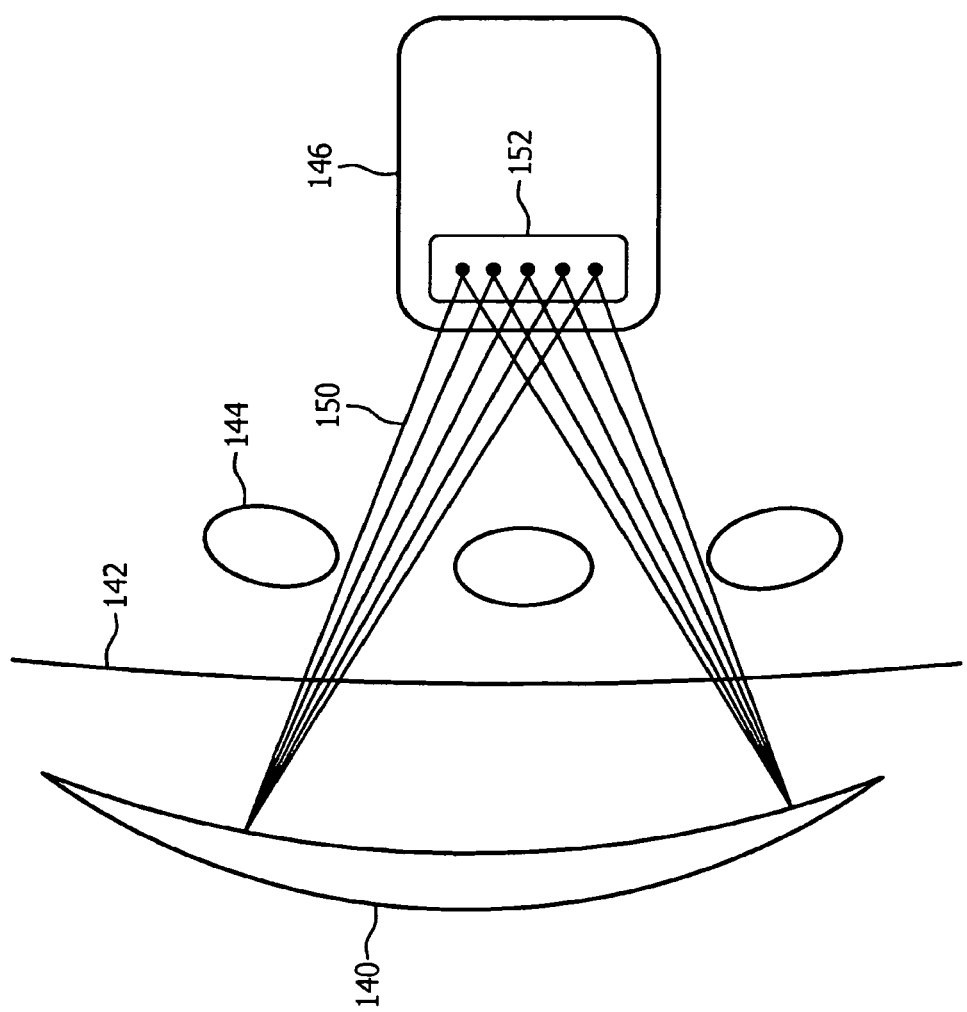
FIG. 5 illustrates an example of superposition amplitude and phase results for ultrasonic waveforms or rays so that multiple zones of the ROI can be ablated concurrently as the HIFU array transmits ultrasonic waves through the patient's skin and past the ribs, minimizing the overall therapy time.

FIG. 5 illustrates an example of superposition amplitude and phase results for ultrasonic waveforms or rays 150 so that multiple zones 152 of the ROI 146 can be ablated concurrently as the HIFU array 140 transmits ultrasonic waves through the patient's skin 142 and past the ribs 144, minimizing the overall therapy time. FIG. 5 illustrates how the multiple zones from the ROI can be accounted for in the optimizations.

The following description is provided by way of example to further detail the operation of the optimization module or function 102 and the related systems and methods of FIGS. 1-5. The HIFU array 140 has transmitter elements (not shown) that are designated by a number n. They each deliver a power $I_n$, part of which is dissipated in the ROI. This part is proportional to the volume integral of the sonic intensity, the local absorption coefficient, and the attenuation of the wave before reaching the ROI. The local intensity inside the ROI, as produced by the wave, is equal to $I_n$. A number $E_{ROI}$ is defined that is proportional to the energy delivered over a given time for a unit of absorption as:

$$E_{ROI} = \sum_n I_n \left| \int_{V_{ROI}} e^{j(\varphi_n - k|\vec{r} - \vec{r_f}|)} dv \right|^2$$

$E_{ROI}$ thus represents the total energy in the ROI, as shown in FIG. 5. The number n corresponds to each of the transducer elements and $I_n$ is the mean acoustic intensity in the ROI, corresponding to each of the transducer elements. The integral over the volume of the ROI takes into account the phase ($\varphi_n$) corresponding to each of the transducer elements, the wave number k and the relative distance $|\vec{r} - \vec{r_f}|$ of the point in the ROI with respect to the natural focus of the transducer.

For the case of all the $I_n$ and $\varphi_n$ (i.e., for all transducers), respectively, being equal, a spherical wave is defined incident through an opening cone defined by the transducer opening. If the focal point is shifted to a new position $\vec{r_{f1}}$, and at the same time the $\varphi_n$ of each transducer is adjusted, the equation is of the same form. This corresponds to the well known effect of moving the focus of an array electronically. For each position of the focus there is a corresponding set of values for the array elements defining a wave function for the wave delivering energy to that point of space.

When using the HIFU system for treatment, ultrasonic energy is applied for several minutes. During this time, heat diffuses from the point or spot being treated. Therefore, the heat need not be applied evenly everywhere: rather, a raster of points can be selected at some distance from each other that is larger than the focal spot. As a result, the interference effects between the spots can be controlled to become small enough to be negligible, such that:

$$E_{ROI} = \sum_{mn} |A_{nm} e^{j(\varphi_{nm} - k|\vec{r_{mn}} - \vec{r_f}|)}|^2$$

As long as the spot being treated is reasonably close to the natural focus of the transducer, within the beamwidths of the individual elements, the $A_{nm}$ amplitude is independent of m. For the case of an unobstructed transducer, the phases are chosen to make $\varphi_{nm} = k|\vec{r_{mn}}| + \alpha_m$. $E_{ROI}$ now becomes the sum over the energy numbers of the volume elements, as expected. The energy becomes independent of the angle α that, as will be shown, can be used for optimizing the more complicated case of obstructions in the near field, e.g. by ribs.

Another parameter that can be used for optimizing the near field is the wave number k, that affects the wavelength and therefore also the diffraction pattern of the waves. k is optimized within the bandwidth of the HIFU transducer, which is 0.5 MHz, according to one embodiment.

For the obstructed case, the energy function is written as:

$$E_{RIB} = \sum_{mn} |B_{nm} e^{j(\beta_{nm} - k|\vec{r_m} - \vec{r_f}|)}|^2$$

Next, $E_{RIB}$ (the energy absorbed by the rib obstruction is minimized. A suitable system of volume elements are chosen covering the ribs for which the amplitudes $B_{nm}$ and phases $\beta_{nm}$ are computed. Furthermore, the energy function corresponding to the intercostal spaces can be written as:

$$E_{ICST} = \sum_{mn} |C_{nm} e^{j(\gamma_{nm} - k|\vec{r_m} - \vec{r_f}|)}|^2$$

While minimizing $E_{RIB}$, the intercostal energy $E_{ICST}$ is maximized. Similar to $E_{RIB}$, a suitable system of volume elements are chosen covering the spaces between ribs for which the amplitudes $C_{nm}$ and phases $\gamma_{nm}$ are computed.

The objective function mentioned above becomes the maximization of $E_{ROI}$ and at the same time the minimization of $E_{RIB}$ and maximization of $E_{ICST}$. It has been shown that suitable Eigenvectors for numerical optimization are represented by giving the same amplitude to all transducer elements. The functions all correspond to focusing the field but to different locations. The phases for the array are computed from said locations, but contain a common non-defined phase. The Eigen-functions are thus completely degenerate in that the energy is independent both of the focal spot position and the common phase.

The system can now be optimized by expressing the heating in the rib region (both in the ribs and in the intercostal spacing) using said Eigen-functions: In the ribs region their degeneracy will be lifted, and by varying the Eigenvalues so that the resulting amplitudes and phases can concurrently ablate multiple zones of the ROI, the overall therapy time is minimized.

In this manner, in MR-guided HIFU procedures that utilize intercostal spaces, an optimal set of transmission parameters (amplitudes and phases) is generated corresponding to a given HIFU transducer position, geometry, and acoustic parameters and also accounting for the ablation ROI size and position and the ribs' locations. Amplitude and phase results can also be super-positioned so that multiple zones of the ROI can be ablated concurrently, minimizing the overall therapy time.

Figure 6:
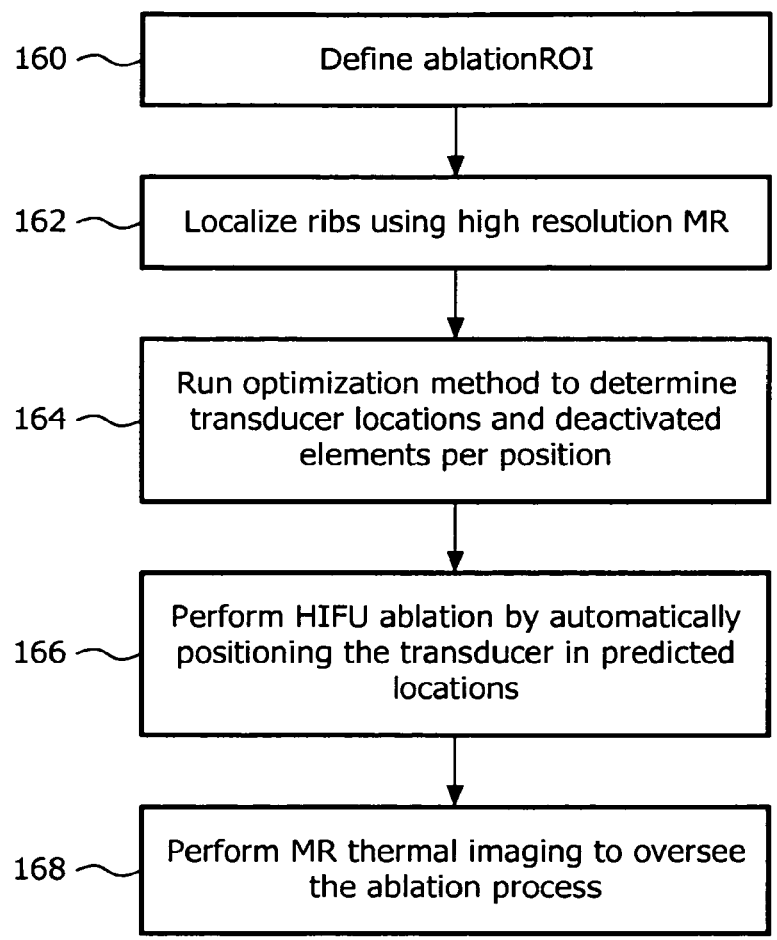
FIG. 6 illustrates a method for optimizing HIFU transducer positioning during MR-guided tissue ablation procedures that utilize intercostal spaces, such as liver ablation.
Figure 7:
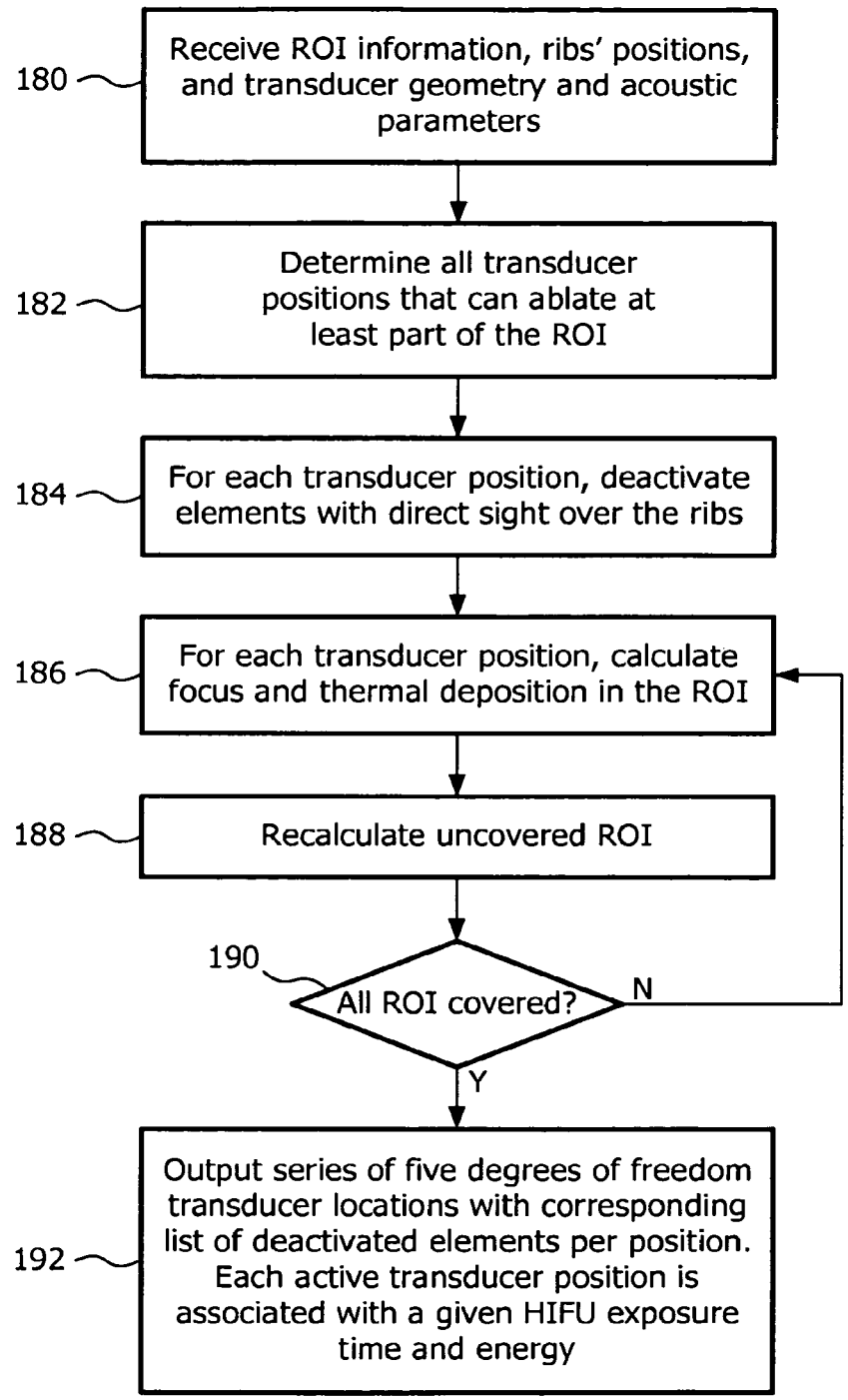
FIG. 7 illustrates a method for optimizing HIFU transducer positioning.
Figure 8:
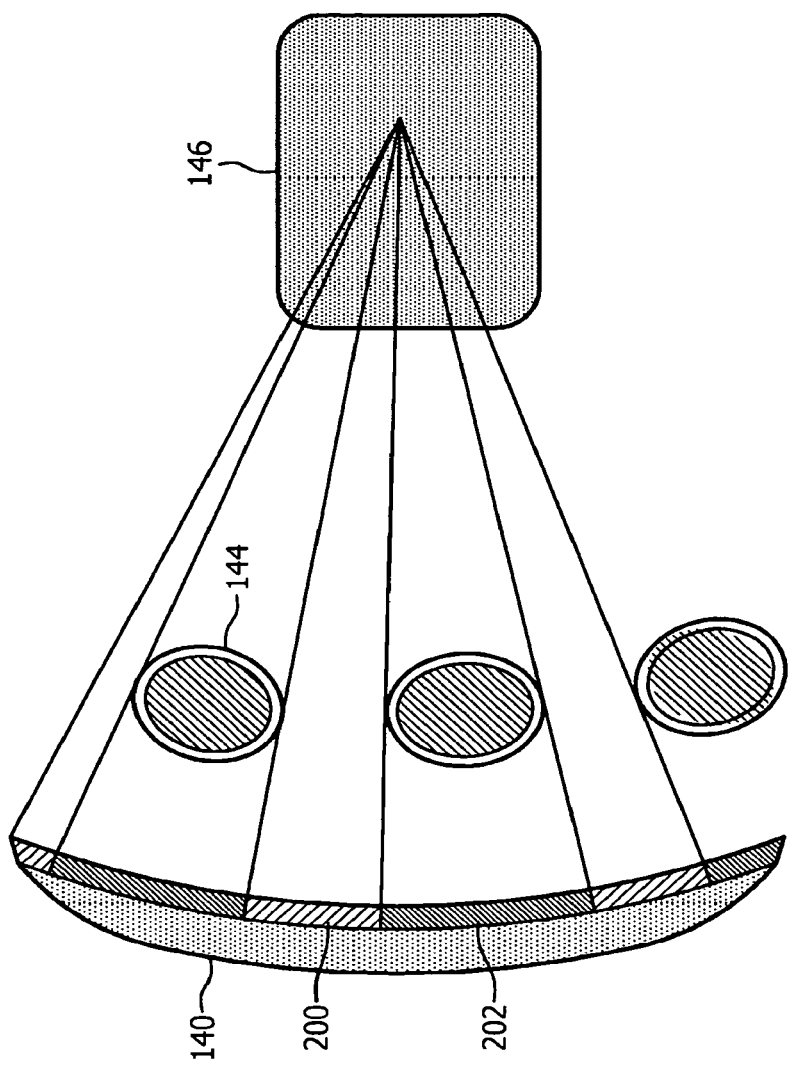
FIG. 8 illustrates a conceptual arrangement with the HIFU array, the ribs, and the ROI for a given position of the array.

FIGS. 6-8 and the related description relate to optimization of transducer position and element deactivation to exploit intercostal spacing during MR-guided tissue ablation. The optimization procedure accounts for the HIFU transducer geometry and acoustic parameters, ablation ROI size and position, as well as ribs' locations in 3D. The optimization also takes the respiratory movement of the organ into account. The ribs' locations may be provided through segmentation of high resolution MR data. The output of the optimization procedure is a series of five-degrees-of-freedom transducer locations (e.g., 3 dimensions plus pitch and yaw) together with a corresponding list of deactivated transducer elements per position. Each transducer position is associated with a given HIFU exposure time and energy such that after sonication from all positions the entire ROI is ablated. In one embodiment, the transducer positions yielded by the optimization procedure are sorted in the descending order of their ROI coverage so that the treatment starts from the position with best coverage. In another embodiment, heating in superficial skin layers is minimized by sorting the transducer positions such that there is minimal overlap between consecutive active aperture footprints.

FIG. 6 illustrates a method for optimizing HIFU transducer positioning during MR-guided tissue ablation procedures that utilize intercostal spaces, such as liver ablation. At 160, the ablation ROI is defined by a user. At 162, high resolution MR imaging is used to segment the ribs. At 164, the ROI information, the ribs' positions, and the transducer geometry and acoustic parameters are used by an optimization procedure or algorithm (e.g., a set of computer-executable instructions), yielding a series of transducer locations together with a corresponding list of deactivated elements at each position. The transducer locations are specified as five-degrees-of-freedom parameters (e.g., three dimensions plus pitch and yaw), and each transducer position is associated with a given HIFU exposure time and energy. At 166, sonication from all positions is carried out so that the entire ROI is ablated. At 168, MR thermal imaging is performed during sonication, to oversee the ablation process.

FIG. 7 illustrates a method for optimizing HIFU transducer positioning, such as occurs at step 164 of FIG. 6. At 180, information related to HIFU transducer geometry and acoustic parameters, ablation ROI size and position, and ribs' locations, are received as input for the optimization algorithm. At 182, all transducer positions from which ultrasonic waves can be emitted to ablate at least a part of ROI are determined based on theoretical acoustic focusing and thermal deposition of the HIFU transducer. At 184, for each of the transducer positions determined at 182, the elements with direct sight over the ribs are deactivated. That is any transducer position from which an ultrasonic wave has a line of sight that passes through a rib on its way to the ablation target is deactivated.

At 186, acoustic focusing and thermal deposition in the ROI are calculated for each transducer position determined at 182, discarding in each case the elements with a line of sight through the ribs. At 188, the transducer position with largest thermal deposition in the ROI is selected. At 190, a determination is made regarding whether the entire ROI is covered (i.e., whether the entire ROI will be ablated by the active transducer positions). If all the ROI is covered, then the optimization is completed and, at 192, the series of active transducer locations is output with a corresponding list of deactivated elements per position. Each active transducer position is associated with a given HIFU exposure time and energy (i.e., dose). If less than all of the ROI is covered, the optimization procedure returns to 186 to select the transducer position with next largest thermal deposition in the remaining uncovered ROI.

FIG. 8 illustrates a conceptual arrangement with the HIFU array 140, the ribs 144, and the ROI 146 for a given position of the array. The ribs are avoided by deactivating elements with direct sight over the ribs. The focusing and thermal deposition is calculated in the ROI considering only the active elements 200, and not deactivated elements 202. In this manner, in MR-guided HIFU procedures that utilize intercostal spaces, a priori planning of the treatment is performed based on the ablation ROI size and position, transducer geometry and acoustic parameters, and the ribs' 3D position. This aspect mitigates a need for manual repositioning of the transducer array based on thermal imaging.

Figure 9:
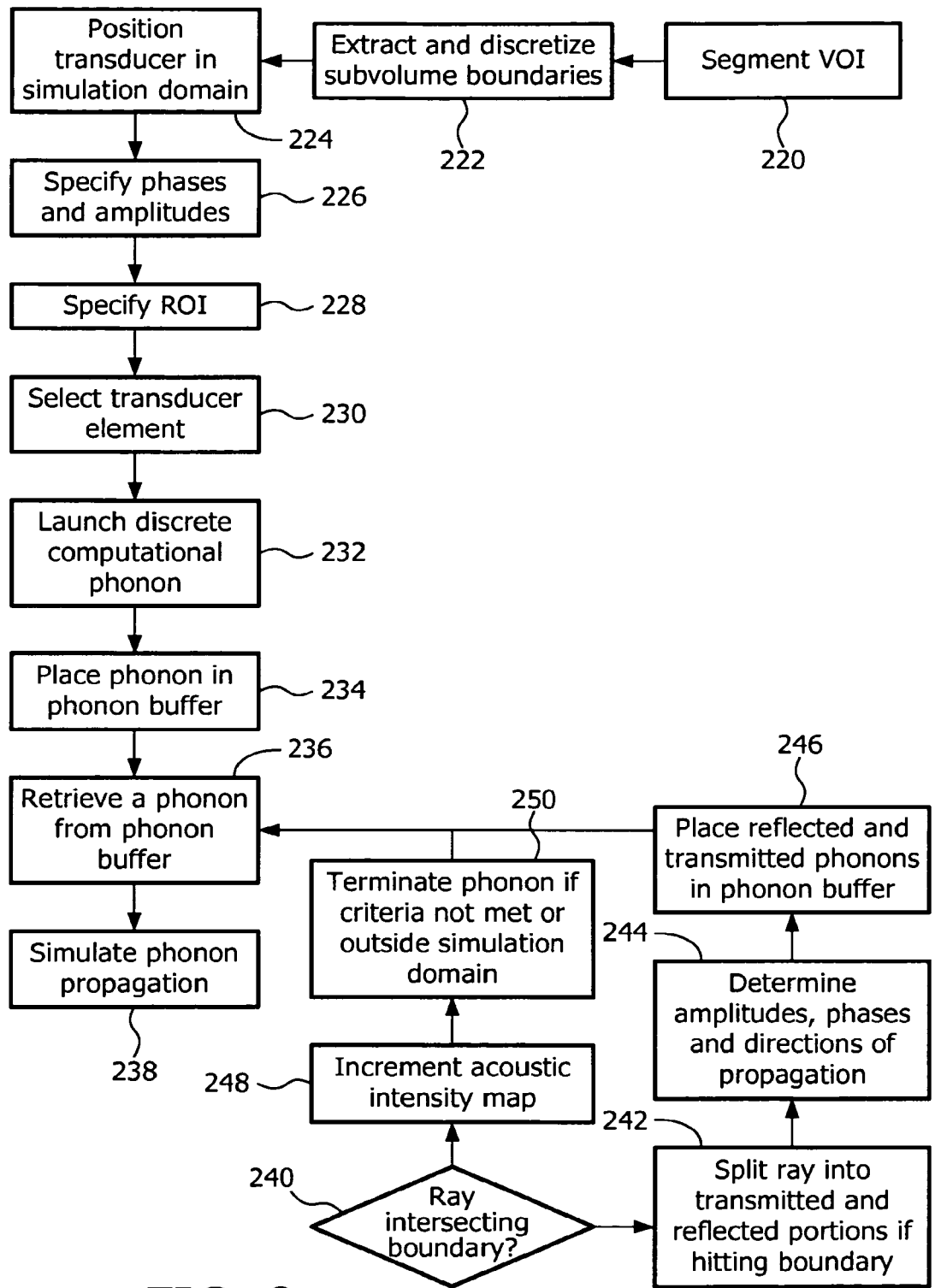
FIG. 9 illustrates a method of performing stochastic acoustic simulation, in accordance with one or more aspects described herein.
Figure 10:
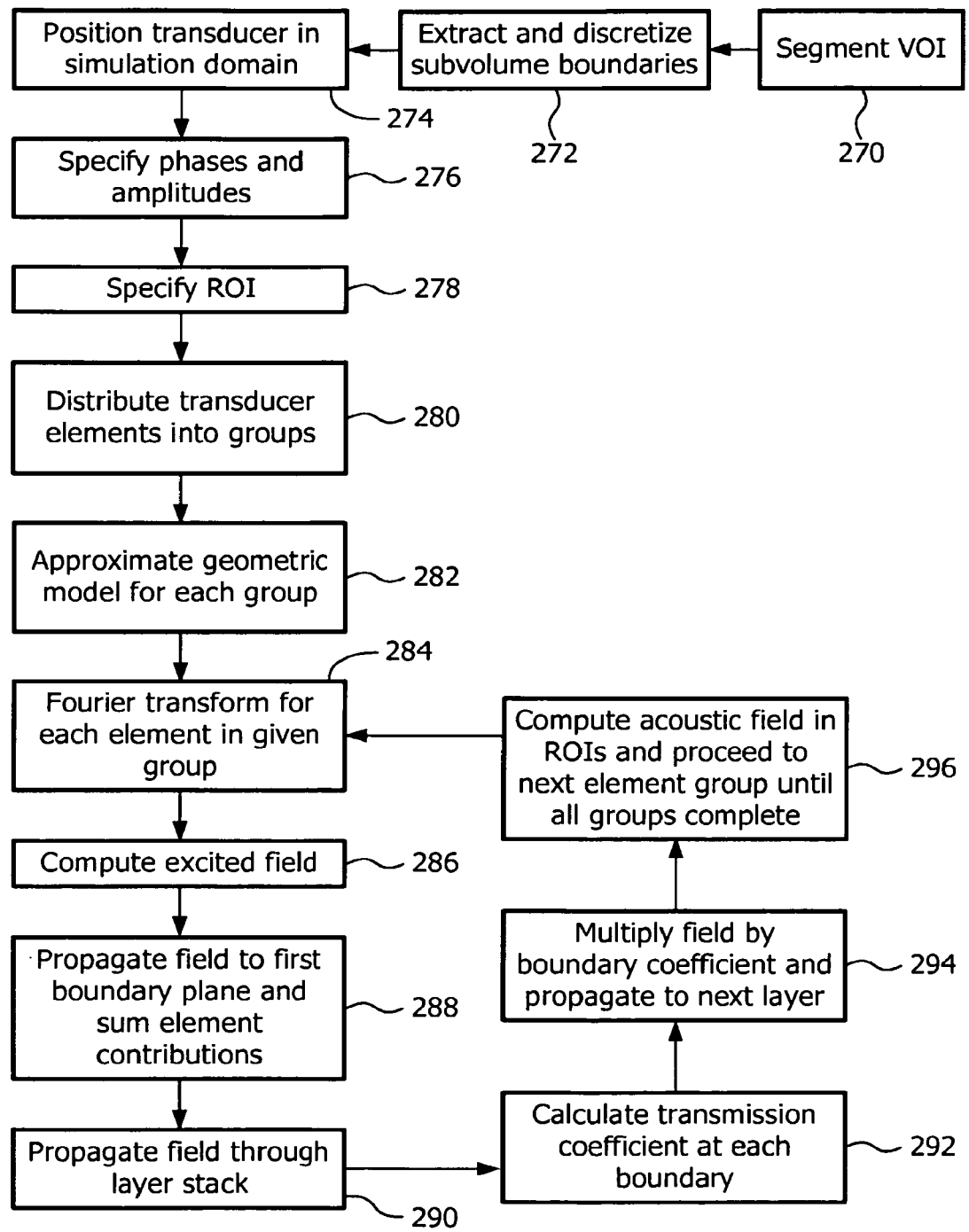
FIG. 10 illustrates a method of performing acoustic simulation with planar approximation, in accordance with one or more aspects described herein.
Figure 11:
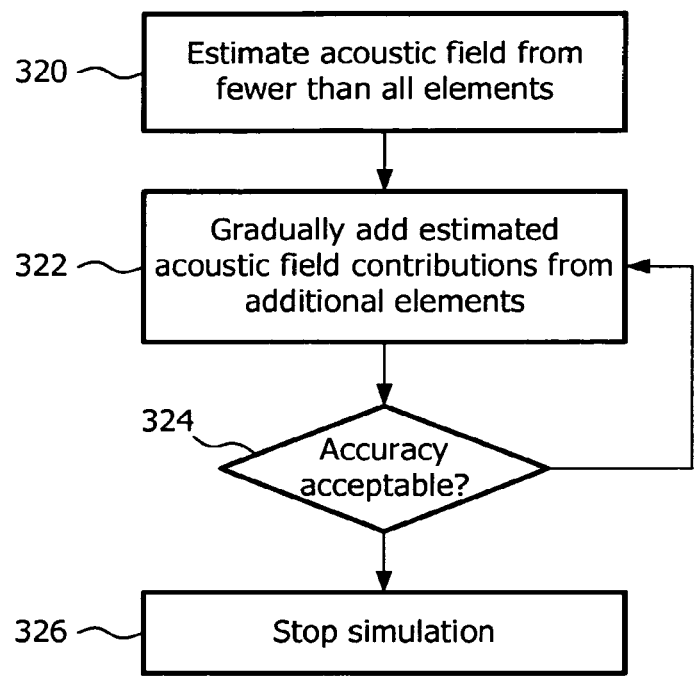
FIG. 11 illustrates a method for estimating the contributions of a subset of all transducer elements, in accordance with one or more aspects described herein.

FIGS. 9-11 and related description further detail various embodiments related to in situ sonication optimization through fast acoustic simulations. In focused ultrasound therapy, the achieved distribution of the thermal energy and accumulated thermal dose depend on the acoustic properties of the tissues within the sonication path. According to one embodiment, fast acoustic in situ simulations with the acoustic path modeled are provided as an interactive tool for optimizing the treatment. These simulations may be carried out immediately before the treatment to optimize the sonication parameters. Proper, patient-specific modeling of the acoustic path improves the positioning and sharpness of the focus. Assuming the speed of sound is known approximately within the different tissues, these simulations can also be used to determine the phase for the different transducer elements in order to achieve a tight focus. Alternatively, the element phase can be changed interactively until the focus quality is sufficient. Working interactively on the tool, the user can optimize the transducer positioning and thermal exposure, taking into account other factors such as heat transferred into nearby organs.

Three algorithms are described in FIGS. 9-11, which enable the above-described functionality. The first algorithm uses stochastic simulation to yield approximate predictions which improve with simulation time. The second algorithm achieves fast calculation by approximating the acoustic path as a stack of planar interfaces. The third algorithm estimates the acoustic field for a subset of transducer elements.

FIG. 9 illustrates a method of performing stochastic acoustic simulation, in accordance with one or more aspects described herein. According to the method, which may be stored on a computer-readable medium as a set of computer-executable instructions, stochastic simulation is used to quickly form a gradually improving estimate of the acoustic field. Discrete acoustic rays are randomly emitted from the transducer elements of a HIFU array, and ray tracing techniques are used to model their propagation towards the ROI. The obtained estimate may be rough at first, and improves with time as more rays are simulated. A user can monitor the estimate in real time and interrupt the simulation when ready to accept or reject the sonication setup.

Accordingly, at 220, a geometric model of a volume of interest (VOI) is segmented with acoustic parameters being specified for each subvolume. The boundary surfaces between subvolumes are extracted and discretized into a computationally suitable data structure, at 222. That is, each subvolume is specified by its respective acoustic parameters and limiting boundary surfaces. The transducer is positioned in the simulation domain, at 224. Phases and amplitudes of individual transducer elements are specified, at 226. Regions of interest in the VOI are specified at 228.

A transducer element is chosen based on a predefined algorithm, at 230. In one embodiment, all elements are analyzed systematically in a predefined order, and the selection is made stochastically based on the relative amplitude of the element. At 232, a discrete computational phonon is launched from the selected transducer element. The direction of the phonon is chosen randomly or pseudo-randomly according to a predefined directivity distribution. In one embodiment, the distribution is based on the directivity pattern of the element. Associated with the phonon are amplitude and phase, which are initialized with those of the transducer element. At 234, the phonon is placed in a phonon buffer.

At 236, a phonon is retrieved from the phonon buffer. If the buffer is empty, the method reverts to 220. At 238, the propagation of the phonon is simulated with ray tracing methods. At 240, it is determined whether the ray intersects with any boundary of the subvolume or a volume of interest.

The phase of the phonon is propagated according to the travelled acoustic distance. If hitting a boundary, the ray is split into a reflected part and a transmitted part, at 242. The amplitudes, phases, and propagation directions are determined based on the angle of incidence and the material parameters of the subvolumes on different sides of the boundary, at 244. According to one embodiment, the propagation directions are determined with the Snell law. In another embodiment, the directions are determined from a directivity distribution. At 246, both (e.g., reflected and transmitted) phonons are placed in the photon simulation buffer, and the method reverts to 236.

If the determination at 240 indicates that the phonon path crosses a volume of interest, the acoustic intensity map of the volume is incremented accordingly, at 248. At 250, the phonon is terminated if the amplitude of the phonon becomes lower than some criterion, or if the trajectory of the phonon takes it outside the simulation domain, and the method reverts to 236. In one embodiment, the phonon buffer is arranged in such way that phonons with lowest amplitudes are chosen first.

FIG. 10 illustrates a method of performing acoustic simulation with planar approximation, in accordance with one or more aspects described herein. According to the method, which may be stored on a computer-readable medium as a set of computer-executable instructions, an acoustic path is approximated as consisting of a stack of homogeneous materials constrained between planar interfaces. Maximal simulation speed is achieved if the same geometry model is used for all transducer elements. For improved accuracy, the transducer elements can be partitioned into element groups, each having their own approximation of the geometry.

At 270, a geometric model of a VOI is segmented with acoustic parameters being specified for each subvolume. The boundary surfaces between subvolumes are extracted and discretized into a computationally suitable data structure, at 272. That is, each subvolume is specified by its respective acoustic parameters and limiting boundary surfaces. The transducer is positioned in the simulation domain, at 274. Phases and amplitudes of individual transducer elements are specified, at 276. Regions of interest in the VOI are specified at 278.

At 280, the transducer elements are distributed into groups. For each group, an approximate geometric model is formed, where the boundary surfaces are approximated with planes, at 282. All the transducer elements belonging to the group are traversed during this step so that an approximate geometric model is formed for each transducer element. At 284, for each element, a Fourier transformation of the source distribution of the element is computed in the natural plane of that element. At 286, the corresponding excited field is computed. The field is propagated to the first boundary plane and the contributions from all elements are summed at 288. The first plane now contains the field excited by the transducer element group.

At 290, the field is propagated through the tissue layer stack. According to one embodiment, if acoustic reflections are weak, as is common for biological tissues, multiply-reflected fields may be disregarded. In this case, the reflected field portions are disregarded and only the transmitted portion of the field is tracked. At each boundary, a transmission coefficient is calculated for each component of the Fourier-transformed field based on the wave vector of the component and the materials parameters on different sides of the boundary, at 292. The field is multiplied with the transmission coefficient, and propagated to the next tissue layer, at 294. The acoustic field is computed in the regions of interest and proceeds to the next transducer element group, at 296.

In an alternate embodiment, if reflections need to be taken into account, but are not very strong, one may resort to an iterative scheme. With each boundary, a transmitted and reflected field is associated. Initially, the first boundary contains the excited field from the transducer element group and all other fields are empty. The fields are updated by computing at each boundary the reflected and transmitted field components and by propagating them to the nearby boundaries. For weak reflections, the iteration converges rapidly.

The algorithm of FIG. 10 thus uses Fast Fourier Transformation for propagating the acoustic field from one surface to another. To illustrate the point, it may be assumed that there are two surfaces, each discretized into N geometric primitives. Then, propagating the field from surface 1 to surface 2 in spatial domain involves $O(N^2)$ computations. However, if the two surfaces are planar, parallel, and uniformly discretized, a Fourier transform is applied to the field in surface 1 with $O(N \log_2 N)$ operations, the Fourier-transformed field is propagated into surface 2 with $O(N)$ operations, and transformed back in $O(N \log_2 N)$ operations. Moreover, if there are several layers, there is no need to carry out Fourier transformations at intermediate layers.

The requirement that all surfaces be flat and parallel is restrictive but may be tolerable for some applications, for example for correcting fat aberration in uterine fibroid treatment. However, the requirement of parallelism can be relaxed somewhat. For instance, the Fourier-transformed field can be propagated into a slightly tilted plane with minimal computational cost. In the conversion, part of the acoustic spectrum may be lost, but this part amounts to waves propagating to the sides and, in the considered application, is usually of little interest. Regarding flatness, the directivity patterns of individual transducer elements tend to be narrow. Hence, at least in the level of a single transducer element, in many application the geometry can be approximated as a stack of layers constrained by planar, although not necessarily parallel, boundaries.

In one embodiment, the algorithm of FIG. 10 can be modified in such way that either the first or the last layer can be strongly reflecting. If the geometry allows for an approximation, where all planes are parallel, multiple reflections can be taken into account in a single iteration. The acoustic field is computed in the volumes of interest and proceeds to the next transducer element group.

In another embodiment, spatially depending reflectivity and transitivity are associated with any boundary. For example, a bone can be modeled by placing a boundary at the center of the bone and specifying a zone of low transitivity across the bone.

FIG. 11 illustrates a method for estimating the contributions of a subset of all transducer elements, in accordance with one or more aspects described herein. At 320, the acoustic field is estimated from a small subset of the transducer elements. At 322, estimated acoustic field contributions from additional elements are gradually added to improve the estimate. The elements are chosen fairly evenly distributed on the transducer surface, such that the intermediate intensity distribution is representative of the final distribution for all transducer elements. At 324, a determination is made regarding whether the desired accuracy has been obtained. If so, the simulation may be interrupted or stopped, at 326. If not, then the method reverts to 322 for addition of further element acoustic field contributions. The phase resonance of the simulated elements can be estimated using this approach, and thus also the focus quality.

The approach of FIG. 11 can be combined with those of either or both of FIGS. 9 and 10, or any other simulation procedure. Appropriate elements are selected from which to simulate the resulting acoustic intensity distribution. By choosing elements that are at a relatively far distance from each other on the transducer surface, the intensity distribution resulting from a few elements is representative of the final distribution of all transducer elements. The simulation may then be terminated at any point once the user is satisfied with the accuracy.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

What is claimed is:

1. A method of performing an in-situ sonication simulation for an MR-guided high intensity focused ultrasound (HIFU) ablation procedure, including:
   generating a patient-specific acoustic path model of a HIFU transducer that includes a plurality of HIFU transducer elements;
   presenting the acoustic path model to a user via a user interface;
   receiving user input regarding adjustments to at least one of (i) a position of one or more of the HIFU transducer elements and/or (ii) a transmission phase and amplitude of the one or more of the HIFU transducer elements; and
   simulating a HIFU sonication of a region of interest (ROI) using the acoustic path model and the user input,
   wherein simulating the HIFU sonication includes:
      segmenting a volume of interest into subvolumes;
      extracting and discretizing boundaries of the subvolumes;
      positioning the HIFU transducer in a simulation domain;
      specifying phases and amplitudes for the HIFU transducer elements in the HIFU transducer;
      specifying one or more regions of interest (ROI) in the volume of interest;
      selecting a first HIFU transducer element from the HIFU transducer elements;
      launching a discrete computational phonon;
      analyzing propagation characteristics of the launched phonon;
      storing the launched phonon and path characteristic data in a phonon buffer that stores path characteristic data for a plurality of phonons;
      retrieving a new phonon from the phonon buffer;
      simulating phonon propagation for the new phonon;
      determining whether a ray defining a path of the new phonon intersects one of the subvolume boundaries;
      dividing the ray into a transmitted portion and a reflected portion if the ray intersects the one of the subvolume boundaries;
      determining amplitude and phase information for each of the transmitted and reflected portions of the ray; and
      storing the amplitude and phase information for each of the transmitted and reflected portions of the ray in the phonon buffer.

2. A method of performing an in-situ sonication simulation for an MR-guided high intensity focused ultrasound (HIFU) ablation procedure, including:
   generating a patient-specific acoustic path model of a HIFU transducer that includes a plurality of HIFU transducer elements;
   presenting the acoustic path model to a user via a user interface;
   receiving user input regarding adjustments to at least one of (i) a position of one or more of the HIFU transducer elements and/or (ii) a transmission phase and amplitude of the one or more of the HIFU transducer elements; and
   simulating a HIFU sonication of a region of interest (ROI) using the acoustic path model and the user input,
   wherein simulating the HIFU sonication includes:
      segmenting a volume of interest into subvolumes;
      extracting and discretizing boundaries of the subvolumes;
      positioning the HIFU transducer in a simulation domain;
      specifying phases and amplitudes for the HIFU transducer elements in the HIFU transducer;
      specifying one or more regions of interest (ROI) in the volume of interest;
      selecting a first HIFU transducer element from the HIFU transducer elements;
      launching a discrete computational phonon;
      analyzing propagation characteristics of the launched phonon;
      simulating phonon propagation for a new phonon;
      determining whether a ray defining a path of the new phonon intersects one of the subvolume boundaries;
      dividing the ray into a transmitted portion and a reflected portion if the ray intersects the one of the subvolume boundaries; and
      determining amplitude and phase information for each of the transmitted and reflected portions of the ray.

* * * * *